(12) United States Patent
Downey

(10) Patent No.: US 7,922,739 B2
(45) Date of Patent: Apr. 12, 2011

(54) SURGICAL INSTRUMENT WITH TRIGGER CONTROL

(76) Inventor: Earl C. Downey, Salt Lake City, UT (US)

( * ) Notice: Subject to any disclaimer, the term of this patent is extended or adjusted under 35 U.S.C. 154(b) by 581 days.

(21) Appl. No.: 10/551,363

(22) PCT Filed: Mar. 24, 2004

(86) PCT No.: PCT/US2004/009093
§ 371 (c)(1),
(2), (4) Date: Sep. 28, 2005

(87) PCT Pub. No.: WO2004/091377
PCT Pub. Date: Oct. 28, 2004

(65) Prior Publication Data
US 2006/0190027 A1 Aug. 24, 2006

(51) Int. Cl.
*A61B 17/32* (2006.01)
*A61B 17/00* (2006.01)

(52) U.S. Cl. .................................. 606/174; 606/205

(58) Field of Classification Search .......... 606/205–210, 606/174; 600/104, 131; 16/430
See application file for complete search history.

(56) References Cited

U.S. PATENT DOCUMENTS

| | | | |
|---|---|---|---|
| 2,959,172 A | 11/1960 | Held | |
| 3,265,429 A * | 8/1966 | Shatt | 294/19.1 |
| 3,819,091 A * | 6/1974 | Hollender | 222/327 |
| 3,993,064 A | 11/1976 | McCarthy et al. | |
| 4,005,897 A * | 2/1977 | Smith | 294/115 |
| 4,043,323 A * | 8/1977 | Komiya | 600/104 |
| 4,226,239 A * | 10/1980 | Polk et al. | 606/141 |
| 4,369,788 A * | 1/1983 | Goald | 606/207 |
| 5,171,249 A | 12/1992 | Stefanchik et al. | |
| 5,217,451 A | 6/1993 | Freitas | |
| 5,258,006 A * | 11/1993 | Rydell et al. | 606/205 |
| 5,281,220 A | 1/1994 | Blake | |
| 5,282,817 A | 2/1994 | Hoogeboom et al. | |
| 5,318,589 A | 6/1994 | Lichtman | |
| 5,355,871 A | 10/1994 | Hurley et al. | |
| 5,368,606 A | 11/1994 | Marlow et al. | |

(Continued)

OTHER PUBLICATIONS

Related U.S. Appl. No. 12/430,777, filed Apr. 27, 2009, Downey.

(Continued)

*Primary Examiner* — Todd E Manahan
(74) *Attorney, Agent, or Firm* — Thorpe North & Western LLP

(57) ABSTRACT

A surgical device 10 with an ergonomic handle 12 and, an elongated tubular portion 18 extending from the ergonomic handle 12 to a functional end 22. The elongated tubular portion 18 has a longitudinal axis 19, and a finger actuator 16 is positioned substantially in line with this axis. Furthermore, the surgical device 10 may also include a rod 20 functionally disposed within the tubular portion 18 along the longitudinal axis 19. The rod 20 may be coupled proximally to the finger actuator 16 and distally to the functional end 22, such that bidirectional pressure applied by the user's finger to the finger actuator 16 along the longitudinal axis 19 manipulates the functional end 22 in a bidirectional manner in response to or in a common direction to the bidirectional pressure. The surgical device 10 may further comprise a ratcheting mechanism 24 to lock the finger actuator 16 in a fixed position, thus locking the functional end 22 in a fixed position. Additionally, the functional end 22 may be free to rotate around the longitudinal axis 19, and the elongated tubular portion 18 may be detachable from the ergonomic handle 12.

21 Claims, 4 Drawing Sheets

U.S. PATENT DOCUMENTS

| | | | |
|---|---|---|---|
| 5,376,094 A | 12/1994 | Kline | |
| 5,456,684 A | 10/1995 | Schmidt et al. | |
| 5,472,439 A | 12/1995 | Hurd | |
| 5,476,099 A | 12/1995 | Robinson et al. | |
| 5,480,409 A | 1/1996 | Riza | |
| 5,498,256 A | 3/1996 | Furnish | |
| 5,501,654 A | 3/1996 | Failla et al. | |
| 5,514,149 A | 5/1996 | Green et al. | |
| 5,549,623 A | 8/1996 | Sharpe et al. | |
| 5,549,636 A | 8/1996 | Li | |
| 5,571,100 A | 11/1996 | Goble et al. | |
| 5,577,654 A | 11/1996 | Bishop | |
| 5,603,723 A | 2/1997 | Aranyi et al. | |
| 5,611,808 A | 3/1997 | Hossain et al. | |
| 5,618,294 A | 4/1997 | Aust et al. | |
| 5,618,303 A | 4/1997 | Marlow et al. | |
| 5,626,608 A * | 5/1997 | Cuny et al. | 606/205 |
| 5,626,609 A | 5/1997 | Zvenyatsky et al. | |
| 5,632,764 A | 5/1997 | Beideman et al. | |
| 5,645,561 A | 7/1997 | Smith et al. | |
| 5,669,875 A | 9/1997 | Van Eerdenburg | |
| 5,683,362 A | 11/1997 | Rowland et al. | |
| 5,718,714 A * | 2/1998 | Livneh | 606/205 |
| 5,735,873 A | 4/1998 | MacLean | |
| 5,762,255 A | 6/1998 | Chrisman et al. | |
| 5,782,749 A | 7/1998 | Riza | |
| 5,782,844 A | 7/1998 | Yoon et al. | |
| 5,797,927 A | 8/1998 | Yoon | |
| 5,807,393 A | 9/1998 | Williamson et al. | |
| 5,810,806 A | 9/1998 | Ritchart et al. | |
| 5,830,231 A | 11/1998 | Geiges, Jr. | |
| 5,865,361 A | 2/1999 | Milliman et al. | |
| 5,868,784 A | 2/1999 | Riza | |
| 5,868,785 A | 2/1999 | Tal et al. | |
| 5,893,874 A | 4/1999 | Bourque et al. | |
| 5,908,436 A | 6/1999 | Cuschieri et al. | |
| 5,947,996 A | 9/1999 | Logeman | |
| 5,976,121 A | 11/1999 | Matern et al. | |
| 6,007,561 A | 12/1999 | Bourque et al. | |
| 6,066,102 A | 5/2000 | Townsend et al. | |
| 6,074,408 A * | 6/2000 | Freeman | 606/205 |
| 6,077,286 A * | 6/2000 | Cuschieri et al. | 606/170 |
| 6,099,537 A | 8/2000 | Sugai et al. | |
| 6,129,740 A | 10/2000 | Michelson | |
| 6,139,555 A | 10/2000 | Hart et al. | |
| 6,261,307 B1 | 7/2001 | Yoon et al. | |
| 6,299,625 B1 | 10/2001 | Bacher | |
| 6,299,630 B1 | 10/2001 | Yamamoto | |
| 6,352,532 B1 | 3/2002 | Kramer et al. | |
| 6,419,675 B1 | 7/2002 | Gallo | |
| 6,428,530 B1 | 8/2002 | Matern et al. | |
| 6,554,828 B2 | 4/2003 | Schneiter | |
| 7,131,970 B2 | 11/2006 | Moses et al. | |
| 2002/0004663 A1 | 1/2002 | Gittings et al. | |
| 2002/173813 A1 | 11/2002 | Peterson et al. | |
| 2004/0199195 A1* | 10/2004 | Dumontelle | 606/184 |
| 2005/0043582 A1 | 2/2005 | Stokes | |
| 2006/0079876 A1 | 4/2006 | Houser et al. | |
| 2006/0241652 A1 | 10/2006 | Doll et al. | |
| 2007/0093856 A1 | 4/2007 | Whitfield et al. | |

OTHER PUBLICATIONS

Related U.S. Appl. No. 11/259,936, filed Oct. 26, 2005, Downey.

* cited by examiner

SURGICAL INSTRUMENT WITH TRIGGER CONTROL

BACKGROUND OF THE INVENTION

1. Field of Invention

The present invention relates generally to medical devices. More particularly, the present invention relates to trigger controlled surgical instruments.

2. Description of Prior Art

Handles for surgical instruments have traditionally been based on a paradigm of design that is decades old, a design that was adopted to facilitate their use in upper airway endoscopy. These instruments are bent such that their handles are as much as 90 degrees out of alignment with their functional ends. The original design was required to allow a user to have a direct line of vision down a sheath into the area where the surgery is performed. With the advent of fiber optics, the requirements for the bent handle design were eliminated. Surgeons today manipulate surgical instruments by means of a video screen, not a direct line of vision down a sheath. Given this change in technology regarding the visual aspects of surgery, it is surprising that the handles of a majority of surgical instruments have remained unchanged.

Surgical instruments with this bent-handle design can be troublesome to use. They require a user to hold their wrist awkwardly for long periods of time, in a position that encourages the development of Carpal Tunnel Syndrome and chronic joint stress. Many users have taken to holding the instruments in a manner not consistent with their design in an attempt to alleviate the pain and fatigue of long procedures.

Additionally, the bent-handle design does not efficiently translate force from the handle to the functional end of the instrument. Force applied to the handle of the instrument is translated to the functional end to perform the desired action. If the handle is bent out of line with the longitudinal axis of the functional end, a portion of the applied force will be translated to movement of the instrument in a direction that is essentially perpendicular to this axis. This undesirable movement may be translated along the instrument to the functional end, thus compromising stability.

In addition to the inefficient translation of force from the handle to the functional end of the instrument, the bent-handle design better facilitates surgeon use of the tool as a functional extension of a users hand.

SUMMARY OF THE INVENTION

The present invention may be described as a surgical device comprising an ergonomic handle having a finger actuator configured to receive a single finger of a user to control an attached, elongated tubular portion extending from the ergonomic handle. The elongated tubular portion may have a longitudinal axis, and the finger actuator may be positioned substantially in line with the longitudinal axis of the tubular portion. Furthermore, the surgical device may also include a rod functionally disposed within the tubular portion along the longitudinal axis. The rod may be coupled proximally to the finger actuator and may be coupled distally to a functional end, such that bidirectional pressure applied by the user's finger to the finger actuator along the longitudinal axis manipulates the functional end in a bidirectional manner in response to or in a common direction to the bidirectional pressure. The surgical device may further comprise a ratcheting mechanism to lock the finger actuator in a fixed position, thus locking the functional end in a fixed position. Additionally, the functional end may be free to rotate around the longitudinal axis, and the elongated tubular portion may be detachable from the ergonomic handle.

Additional features and advantages of the invention will be apparent from the detailed description which follows, taken in conjunction with the accompanying drawings, which together illustrate, by way of example, features of the invention.

DETAILED DESCRIPTION

Figure 1:
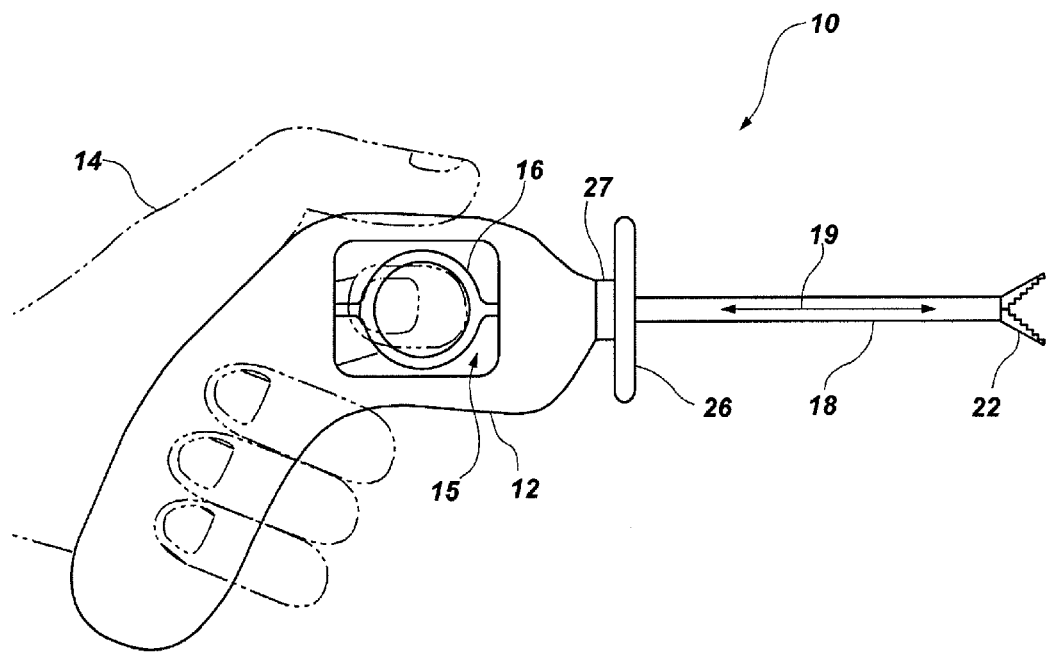
FIG. 1 is a perspective view of a surgical device in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Figure 2:
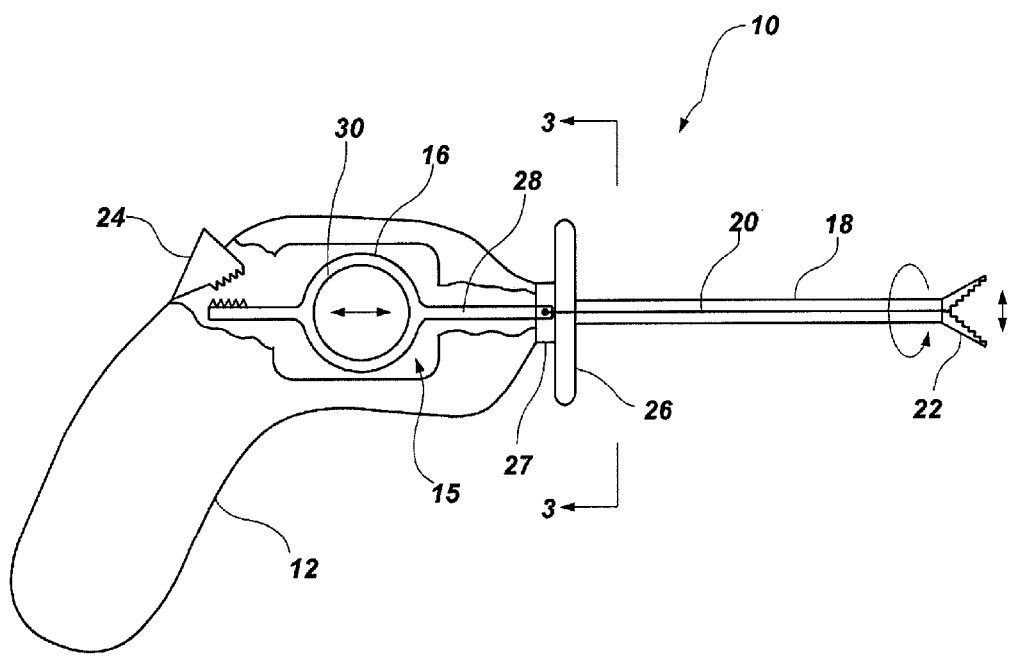
FIG. 2 is perspective view of a surgical device in accordance with an embodiment of the present invention.

The present invention may be embodied as a surgical device as shown in FIG. 1 and FIG. 2. The surgical device 10 may have an ergonomic handle 12, shaped to conform to a user's hand 14 held in a relaxed functional position, thus reducing hand and wrist strain that ultimately leads to Carpal Tunnel Syndrome and chronic joint stress. The ergonomic handle may comprise a sidewall having a handle aperture 15 formed therein, and may be in the shape of a pistol grip, or any other shape that allows the user's hand 14 to be held in a relaxed position. The surgical device may also include a finger actuator 16, having a translating shaft 28 and a finger receiving portion 30 or section 30, configured to receive a single finger (ideally the index finger) of a user through the handle aperture 15.

The surgical device 10 may further include an elongated tubular portion 18 extending from the ergonomic handle 12, and having a longitudinal axis 19. The finger actuator 16 may be positioned substantially in line with the longitudinal axis 19 of the elongated tubular portion 18. Furthermore, a rod 20 may be functionally disposed within the tubular portion 18 along the longitudinal axis 19 that is coupled proximally to the finger actuator 16 and may be coupled distally to a functional end 22. The functional end may be coupled to any surgical end piece known to one skilled in the art, such as, but not limited to, a grasper, scissors, a blade, a laser or a needle holder. The alignment of the user's finger, the elongated tubular portion 18, and the functional end 22 along the same longitudinal axis 19 may allow the functional end 22 to act more as a functional extension of the user's finger than previous designs. Additionally, bidirectional pressure applied by the user's finger to the finger actuator 16 along the longitudinal axis 19 will manipulate the functional end 22 in a bidirectional manner. In other words, movement by the user's finger in one direction along the longitudinal axis 19 will operate the functional end 22 in one direction, while movement by the user's finger in the opposite direction along the longitudinal axis 19 will operate the functional end 22 in the opposite direction.

The surgical device 10 may also include a ratcheting mechanism 24 to lock the finger actuator 16 in a fixed position, thus locking the functional end 22 in a fixed position. The ratcheting mechanism 24 may be positioned near the user's thumb in any position convenient on the handle (side, bottom, or top) for easy accessibility, and it may be operated by pushing, pulling, sliding, or any other functional means of actuation known to one skilled in the art.

Figure 3:
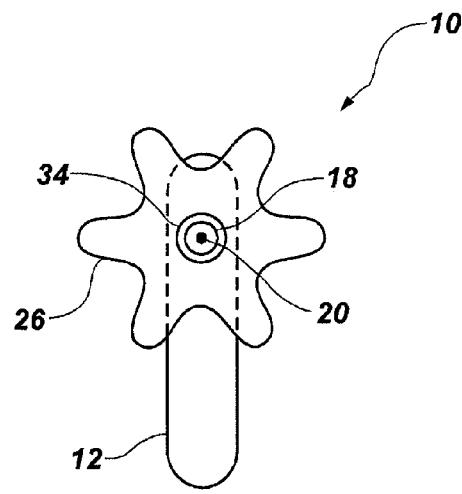
FIG. 3 is a cross-sectional view of the surgical device of FIG. 2.

It may be useful for the functional end 22 to be free to rotate around the longitudinal axis of the elongated tubular portion 18. This can be accomplished by means of a roticulator 26. The roticulator 26 may be attached to the ergonomic handle 12 by a rotateable connection 27. The rotatable connection 27 may be any connection known to one skilled in the art that allows the roticulator 26 to be coupled to the ergonomic handle 12 and that allows rotation around the longitudinal axis 19. As shown in FIG. 3, the roticulator 26 may be a generally disk-shaped structure attached to the elongated tubular portion 18. The example embodiment in FIG. 3 shows a roticulator 26 with notches designed to allow easy rotation by the user's finger. The roticulator 26 may be of any shape, however, that allows rotation by the user's finger. This allows the user to rotate the roticulator 26, which in turn rotates the elongated tubular portion 18 and the functional end 22.

Figure 4:
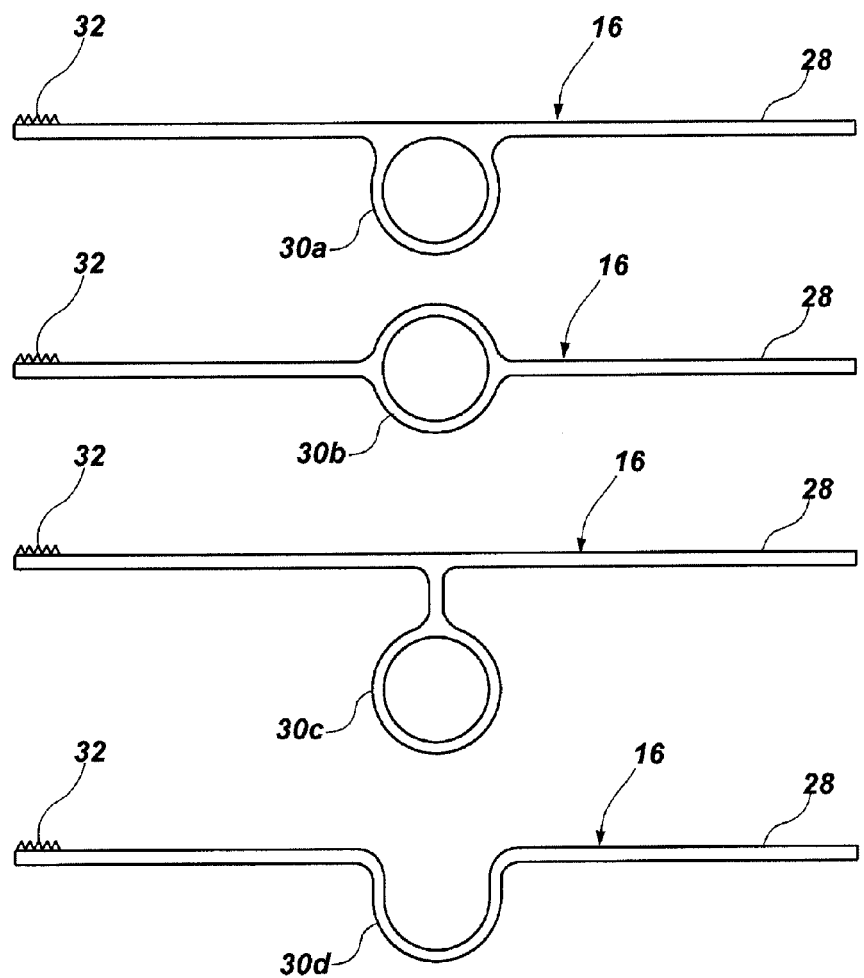
FIG. 4 is a perspective view of examples of finger actuators in accordance with an embodiment of the present invention.

As shown in FIG. 4, the finger actuator 16 may be configured in a variety of ways. These configurations should not be seen as limiting the number of ways that the finger actuator 16 may be constructed, but as examples showing possible variations. Generally, they may consist of a translating shaft 28 with a finger receiving section 30*a,b,c,d* to allow the user to slide the translating shaft 28 along the longitudinal axis 19 of the elongate tubular portion 18 (see FIG. 1). Configuration 30*b* is deemed to be the preferred embodiment because the actuator 16 is fully symmetrical about axis 19. In embodiments utilizing the ratcheting mechanism 24 (see FIG. 2), ratcheting teeth 32 may be disposed on one end of the translating shaft 28 to engage the ratcheting mechanism 24. As further illustrated in FIG. 4, the translating shaft 28 of the finger actuator 16 extends in opposing directions away from the finger receiving section 30. Specifically, the translating shaft 28 is shown as extending in a forward direction away from the finger receiving section 30, and in a rearward direction away from the finger receiving section 30, along the same axis. The translating shaft 28 is configured to extend, in one or both directions, at least partially beyond the handle aperture formed in the sidewall of the ergonomic handle (see FIGS. 1 and 2).

Figure 5:
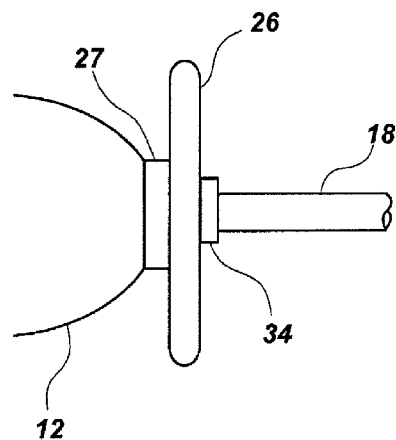
FIG. 5 is a perspective view of a roticulator attachment in accordance with an embodiment of the present invention.

As shown in FIG. 5, it may also be useful for the elongated tubular portion 18 to be detachable from the ergonomic handle 12. This would allow quick changes of instruments associated with the functional end 22, and facilitate cleaning and autoclaving of the individual parts of the surgical device 10 to remove all biological matter after use. In one example embodiment this may be accomplished by a detachable connection 34 between the elongated tubular portion 18 and the roticulator 26. This detachable connection 34 may be by any detachment means known to one skilled in the art, including, but not limited to, a threaded connection or a ring lock connection.

Figure 6:
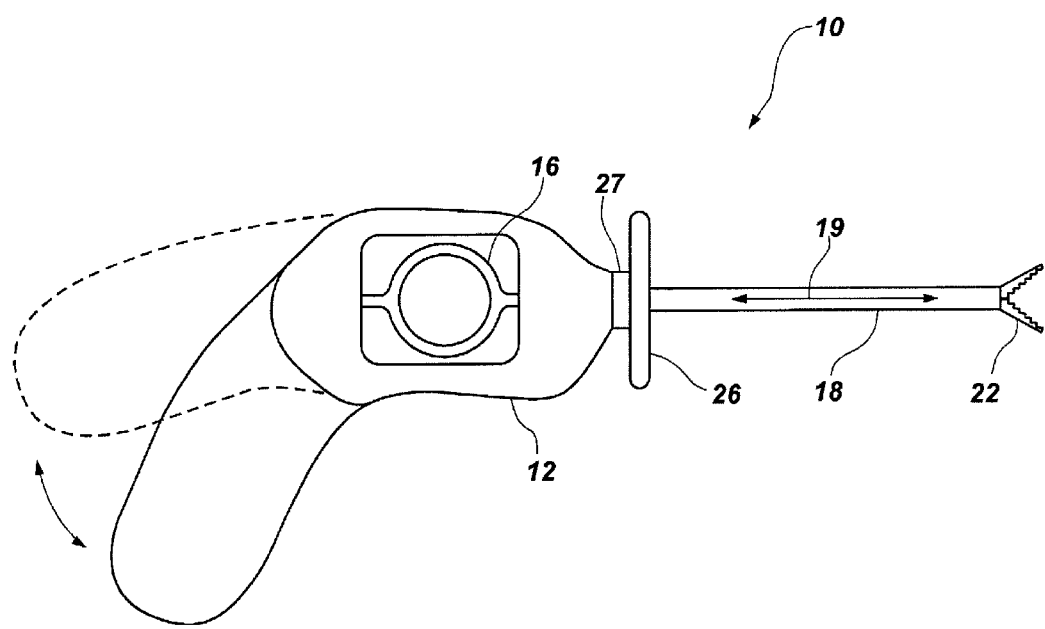
FIG. 6 is a perspective view of a surgical device in accordance with an embodiment of the present invention.

As shown in FIG. 6, a portion of the ergonomic handle 12 that may be substantially out of line with the longitudinal axis 19 can be manipulated about a rotational axis 38 into a position that is substantially in line with the longitudinal axis 19. As an example, this rotation may be accomplished by a means for rotation located at the rotational axis 38, such as a pin, screw, grommet, hinge, or other means know to one skilled in the art. Care must be taken to avoid interference between the means for rotation and the finger actuator 16. As an example, this may be accomplished by placing the rotation mean out of line with the longitudinal axis of the finger actuator 16. It may also be accomplished by utilizing multiple rotational means attached to both sides of the ergonomic handle 12 at the position shown for the rotational axis 38 in FIG. 6 that do not extend through the ergonomic handle 12 to interfere with the finger actuator 16. The rotational manipulation reduces tangling that may occur between the ergonomic handle 12 and other cables and cords in the surgical area. Additionally, a portion of the ergonomic handle 12 that may be substantially out of line with the longitudinal axis 19 can be removed, thus achieving the same tangling reduction result.

Figure 7:
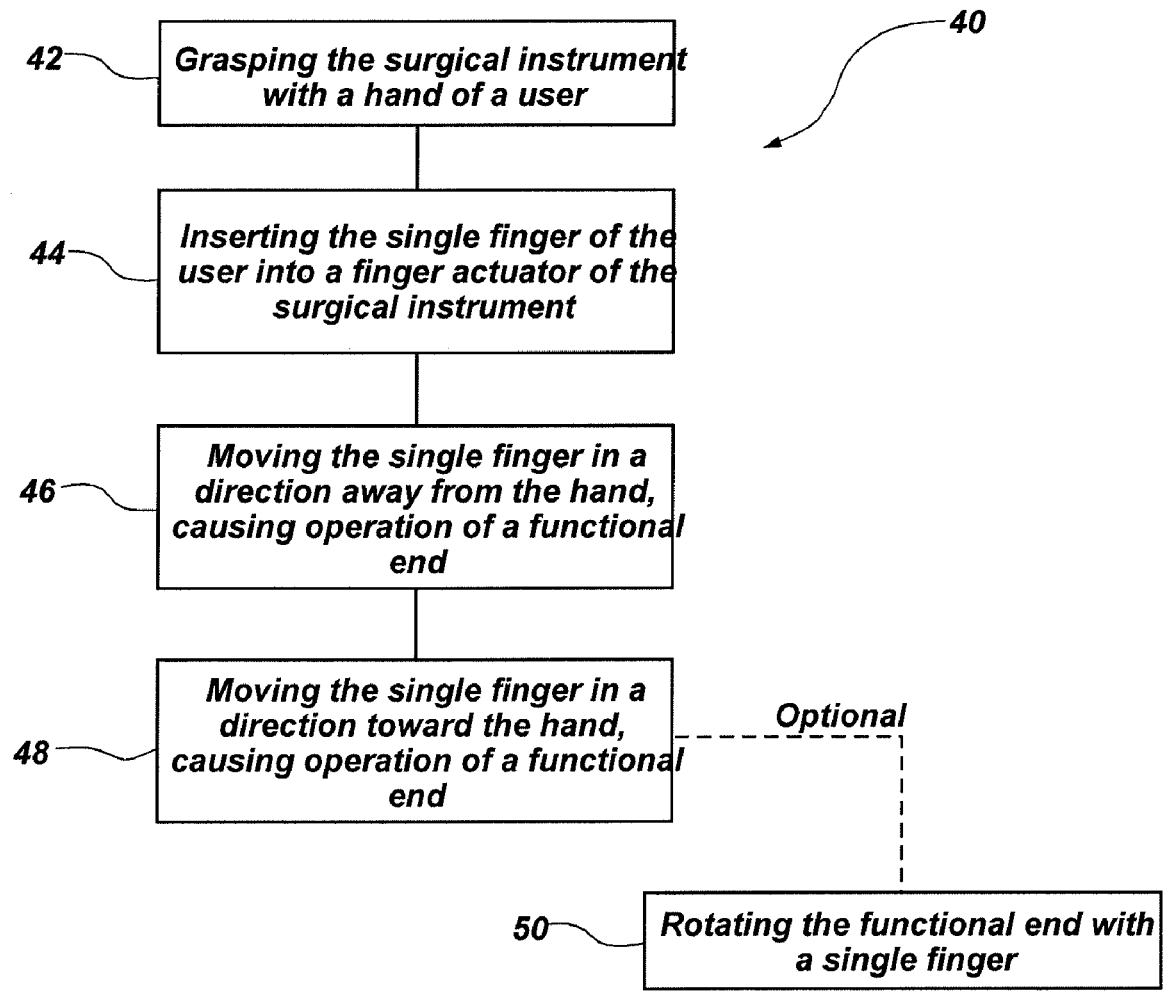
FIG. 7 is a flow chart of a method of manipulating a surgical instrument with a single finger according to an embodiment of the present invention.

FIG. 7 is a flow chart of a method 40 of manipulating a surgical instrument with a single finger according to an embodiment of the present invention. The first step 42 of the method 40 may include grasping the surgical instrument with a hand of a user. Another step 44 of the method 40 may include inserting a single finger (ideally the index finger) of the user into a finger actuator of the surgical instrument. Yet another step 46 of the method 40 may include moving the single finger in a direction away from the hand, causing operation of a functional end. The method 40 may additionally or alternatively include the step 48 of moving the single finger in a direction toward the hand, causing operation of the functional end. Additionally, the method 40 may include the optional step 50 of rotating the functional end with the single finger.

It is to be understood that the above-referenced arrangements are illustrative of the application for the principles of the present invention. Numerous modifications and alternative arrangements can be devised without departing from the spirit and scope of the present invention while the present invention has been shown in the drawings and described above in connection with the exemplary embodiments(s) of the invention. It will be apparent to those of ordinary skill in the art that numerous modifications can be made without departing from the principles and concepts of the invention as set forth in the claims.

What is claimed is:

1. A surgical device, comprising:
an ergonomic handle having an upper portion and a grip portion, the upper portion having a handle aperture formed in a sidewall and accessible by a single finger of a user;
a finger actuator having an actuating finger receiving portion within and accessible through the handle aperture, and a translating shaft that extends in a forward direction from the finger receiving portion, and in a rearward direction from the finger receiving portion beyond the handle aperture along the same axis;
an elongated tubular portion extending from the ergonomic handle and having a longitudinal axis; and
a rod functionally disposed within the tubular portion along the longitudinal axis, the rod being directly coupled proximally to the translating shaft of the finger actuator and distally to a functional end, wherein the finger actuator moves in a non-pivoting, linear manner to directly effectuate an equidistant linear movement of the rod while maintaining a hand of the user about the ergonomic handle in a position consistent with a functional position of the hand.

2. A surgical device as in claim 1, further comprising a functional end coupled to a distal end of the rod, such that bidirectional pressure applied by the single finger to the finger actuator along the longitudinal axis manipulates the functional end in a bidirectional manner in a common direction to the bidirectional pressure.

3. A surgical device as in claim 2, further comprising a ratcheting mechanism supported on the translating shaft to lock the finger actuator in a fixed position, thus locking the functional end in a fixed position.

4. A surgical device as in claim 2, wherein the functional end is free to rotate around the longitudinal axis.

5. A surgical device as in claim 2, wherein the functional end is selected from the group consisting of a grasper, scissors, a blade, a laser and a needle holder.

6. A surgical device as in claim 2, wherein the functional end is a grasper.

7. A surgical device as in claim 2, wherein the functional end is scissors.

8. A surgical device as in claim 1, wherein the elongated tubular portion is detachable from the ergonomic handle.

9. A surgical device as in claim 1, wherein the ergonomic handle has a shape of a pistol grip.

10. A surgical device as in claim 9, wherein a portion of the pistol grip that is substantially out of line with the longitudinal axis can be manipulated into a position that is substantially in line with the longitudinal axis.

11. A surgical device as in claim 9, wherein a portion of the pistol grip that is substantially out of line with the longitudinal axis is detachable.

12. A surgical system operated by a single finger, comprising:
    an ergonomic handle having an upper portion and a grip portion, the upper portion having a handle aperture formed in a sidewall and accessible by a single finger of a user:
    a finger actuator having an actuating finger receiving portion within and accessible through the handle aperture, and a translating shaft that extends in a forward direction from the finger receiving portion, and in a rearward direction from the finger receiving portion beyond the handle aperture along the same axis;
    an elongated tubular portion extending from the ergonomic handle and having a longitudinal axis, the translating shaft of the finger actuator being positioned substantially in line with the longitudinal axis of the tubular portion; and
    a rod functionally disposed within the tubular portion along the longitudinal axis, the rod being directly coupled proximally to the translating shaft of the finger actuator and coupled distally to a functional end, such that bidirectional pressure applied by the single finger to the finger receiving portion of the finger actuator to move the translating shaft in a non-pivoting, linear manner along the longitudinal axis manipulates the functional end in a bidirectional manner in a common direction to the bidirectional pressure.

13. A surgical system as in claim 12, further comprising a ratcheting mechanism supported on the translating shaft to lock the finger actuator in a fixed position, thus locking the functional end in a fixed position.

14. A surgical system as in claim 12, wherein the functional end is free to rotate around the longitudinal axis.

15. A surgical system as in claim 12, wherein the elongated tubular portion is detachable from the ergonomic handle.

16. A surgical system as in claim 12, wherein the functional end is selected from the group consisting of a grasper, scissors, a blade, a laser and a needle holder.

17. A surgical system as in claim 12, wherein the functional end is a grasper.

18. A surgical system as in claim 12, wherein the functional end is scissors.

19. A method of manipulating a surgical instrument with a single finger, comprising the following steps:
    grasping the surgical instrument with a hand of a user;
    inserting the single finger of the user into a finger receiving portion of a finger actuator located within and accessible through a handle aperture of an ergonomic handle of the surgical instrument the finger actuator further comprising a translating shaft that extends in a forward direction from the finger receiving portion, and in a rearward direction from the finger receiving portion beyond the handle aperture along the same axis;
    moving the single finger in a direction away from the hand, causing the finger actuator to move in a non-pivoting, linear manner away from the hand to directly effectuate operation of a functional end while continually maintaining a hand of the user in a functional position about the ergonomic handle; and
    moving the single finger in a direction toward the hand, causing the finger actuator to move in a non-pivoting, linear manner toward the hand to directly effectuate operation of the functional end while further continually maintaining the hand of the user about the ergonomic handle in a position consistent with a functional position of the hand.

20. A method of manipulating a surgical instrument with a single finger as in claim 19, further comprising the step of actuating a roticulator with the single finger to rotate the functional end.

21. A surgical device, comprising:
    an ergonomic handle having an upper portion and a grip portion, and a finger receiving portion of a finger actuator disposed within the upper portion and accessible to a single finger of a grasping hand through a handle aperture formed in a sidewall of the upper portion, the finger actuator further comprising a translating shaft that extends in a forward direction from the finger receiving portion, and in a rearward direction from the finger receiving portion beyond the handle aperture along the same axis;
    an elongated tubular portion extending from the upper portion of the ergonomic handle and having a longitudinal axis, the finger actuator being positioned substantially in line with the longitudinal axis of the tubular portion; and
    a rod functionally disposed within the tubular portion along the longitudinal axis, the rod being coupled proximally to the finger actuator and distally to a functional end.

* * * * *